United States Patent
Brommersma

(10) Patent No.: US 9,833,128 B2
(45) Date of Patent: Dec. 5, 2017

(54) STOPCOCK

(71) Applicant: OLYMPUS WINTER & IBE GMBH, Hamburg (DE)

(72) Inventor: Pieter Brommersma, Bargteheide (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 15/109,697

(22) PCT Filed: Feb. 10, 2015

(86) PCT No.: PCT/EP2015/000284
§ 371 (c)(1),
(2) Date: Jul. 5, 2016

(87) PCT Pub. No.: WO2015/124273
PCT Pub. Date: Aug. 27, 2015

(65) Prior Publication Data
US 2016/0309991 A1   Oct. 27, 2016

(30) Foreign Application Priority Data

Feb. 19, 2014  (DE) .................. 10 2014 002 158

(51) Int. Cl.
*F16K 27/06*  (2006.01)
*F16K 5/02*  (2006.01)
(Continued)

(52) U.S. Cl.
CPC ...... *A61B 1/00137* (2013.01); *A61B 1/00068* (2013.01); *A61M 39/22* (2013.01);
(Continued)

(58) Field of Classification Search
CPC ........... A61B 1/00068; A61B 1/00137; A61M 39/22; A61M 2039/229; F16K 31/602; F16K 5/166; F16K 5/0292; F16K 27/062
(Continued)

(56) References Cited

U.S. PATENT DOCUMENTS 1,002,428 A * 9/1911 Mueller ............... F16K 27/067
                                                251/309
1,354,460 A * 9/1920 Heylman ............. F16K 41/026
                                                251/312
(Continued)

FOREIGN PATENT DOCUMENTS

DE        492954 C    6/1930
DE       1760452 U    1/1958
(Continued)

OTHER PUBLICATIONS

Apr. 24, 2015 International Search Report issued in International Patent Application No. PCT/EP2015/000284.
(Continued)

*Primary Examiner* — Jessica Cahill
*Assistant Examiner* — Josephine Trinidad-Borges
(74) *Attorney, Agent, or Firm* — Oliff PLC

(57) ABSTRACT

A stopcock for a channel that guides a flux medium in a medical endoscope, the stopcock having a housing accommodating a plug rotatable about an axis in a conical seat penetrated by the channel, wherein the housing has a bearing collar adjacent to the conical seat in the direction of the axis, in which bearing collar a handle body is mounted to be rotatable about the axis, the handle body supporting a handle outside the housing and rotationally coupled to the plug displaceable in direction of the axis and resiliently supported relative thereto, wherein the handle body has a radially elastic detent device engaging a circumferential inner groove of the bearing collar to be locking in direction of the axis, wherein the plug is arranged and configured bring the detent device out of engagement with the bearing collar upon displacement in direction of the axis into an unlocked position.

5 Claims, 3 Drawing Sheets

(51) Int. Cl.
  *F16K 5/16* (2006.01)
  *F16K 31/60* (2006.01)
  *A61B 1/00* (2006.01)
  *A61M 39/22* (2006.01)

(52) U.S. Cl.
  CPC ............ *F16K 5/0292* (2013.01); *F16K 5/166* (2013.01); *F16K 27/062* (2013.01); *F16K 31/602* (2013.01); *A61M 2039/229* (2013.01)

(58) Field of Classification Search
  USPC ......... 251/309, 312, 904; 137/15.24, 315.25, 137/315.26
  See application file for complete search history.

(56) References Cited

U.S. PATENT DOCUMENTS

| | | | |
|---|---|---|---|
| 3,779,513 A | 12/1973 | Levine | |
| 3,788,599 A | 1/1974 | Cloyd | |
| 3,882,935 A * | 5/1975 | Calhoun | E21B 34/106 166/322 |
| 3,886,967 A * | 6/1975 | Nelson | E21B 34/102 137/495 |
| 6,708,948 B2 * | 3/2004 | Nosel | F16K 5/02 251/288 |
| 2001/0025942 A1 | 10/2001 | Lotz et al. | |
| 2002/0179878 A1 | 12/2002 | Nosel | |
| 2011/0253925 A1 | 10/2011 | Guo | |

FOREIGN PATENT DOCUMENTS

| | | |
|---|---|---|
| DE | 4226770 A1 | 5/1994 |
| DE | 19819814 C1 | 6/1999 |
| DE | 20005691 U1 | 6/2000 |
| DE | 10126540 A1 | 12/2002 |
| EP | 3733836 A1 | 9/1996 |
| GB | 159666 A | 3/1921 |

OTHER PUBLICATIONS

Aug. 23, 2016 International Preliminary Report on Patentability issued in International Patent Application No. PCT/EP2015/000284.

* cited by examiner

STOPCOCK

The invention relates to a stopcock of the type set forth in the preamble of claim 1.

Such a stopcock is seated on a medical endoscope, which must be kept strictly sterile. This also applies to the stopcock, which must be cleaned and sterilized after every use of the endoscope. In the stopcock, the plug is pressed with the conical surface thereof against the conical seat of the housing. This large surface area of contact cannot be cleaned in the assembled state. Cleaning and sterilization thus necessitates disassembly of the stopcock. This must be done after every use of the stopcock.

A generic stopcock is disclosed in DE 101 26 540 A1. In a housing, the stopcock has a plug and a handle body coupled thereto. The handle body is supported against the housing in the axial direction via a snap ring. After removal of this barrier, the plug and the handle body can be taken out from the housing. However, this construction is disadvantageous in that so doing requires destroying the handle body at the location of the snap ring, which serves as an intended breaking point.

The present invention addresses the problem of providing a generic stopcock so as to allow for easy and non-destructive disassembly.

According to the invention, the detent device can be disengaged, following which the handle body and the plug can then be taken out from the housing. The unlocking is done by acting on the plug during displacement thereof in the direction of the axis. This is possible with the generic construction, because there the handle body and the plug are coupled so as to be displaceable relative to one another in the direction of the axis.

The detent device may be configured in a variety of manners with locking bolts or the like. Preferably, the detent device is configured as a snap ring, which is mounted in a circumferential outer groove of the handle body, this also being known per se from the aforementioned publication.

The disengagement of the detent device may be performed in a variety of manners. Arranged on the plug are cams that expand the snap ring from the inside out when the plug is displaced axially into an unlocked position, until the snap ring is brought out of an engagement with the outer groove of the plug. The handle body is thereby unlocked and can now be removed from the housing together with the plug.

Therein, the cams are configured on fingers that grip between fingers of the handle body. This ensures that the plug and handle body can be interlocked in the same manner as is required to lock the snap ring, and the interlocking fingers guarantee a rotation-preventing positive locking between the plug and the handle body. A run-on slope is configured on cams in each of the two directions of possible displacement. Thus, the cams can not only unlock the snap ring when displaced in one direction in order to be able to disassemble the stopcock, but also in the other direction, for the purpose of assembly.

The drawings schematically depict the invention by way of example.

Figure 1:
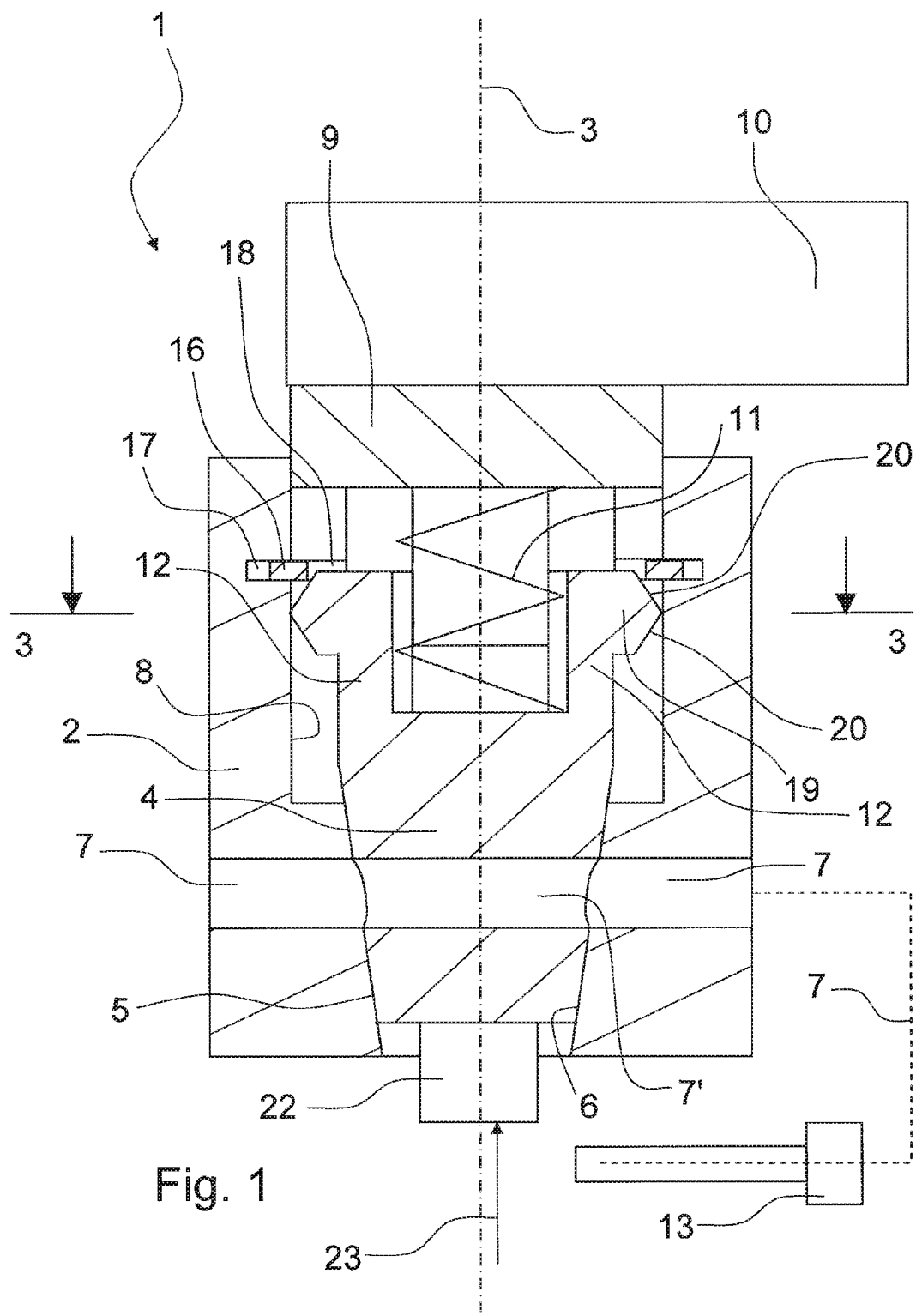
FIG. 1 illustrates an axial section through a stopcock according to the invention, in the angular position according to line 1-1 in FIG. 3
Figure 2:
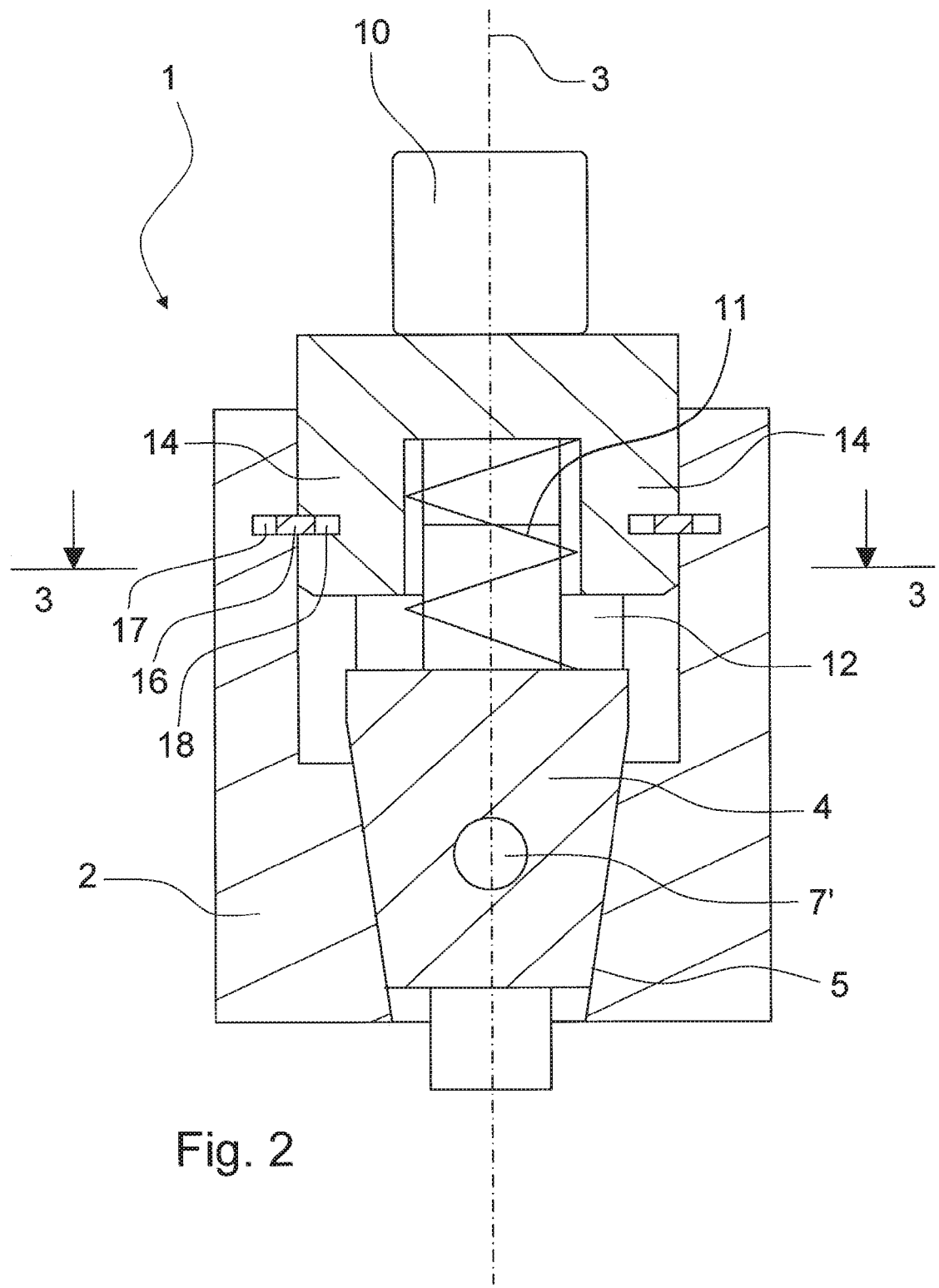
FIG. 2 illustrates an axial section through a stopcock according to the invention, in the angular position according to line 2-2 in FIG. 3.
Figure 3:
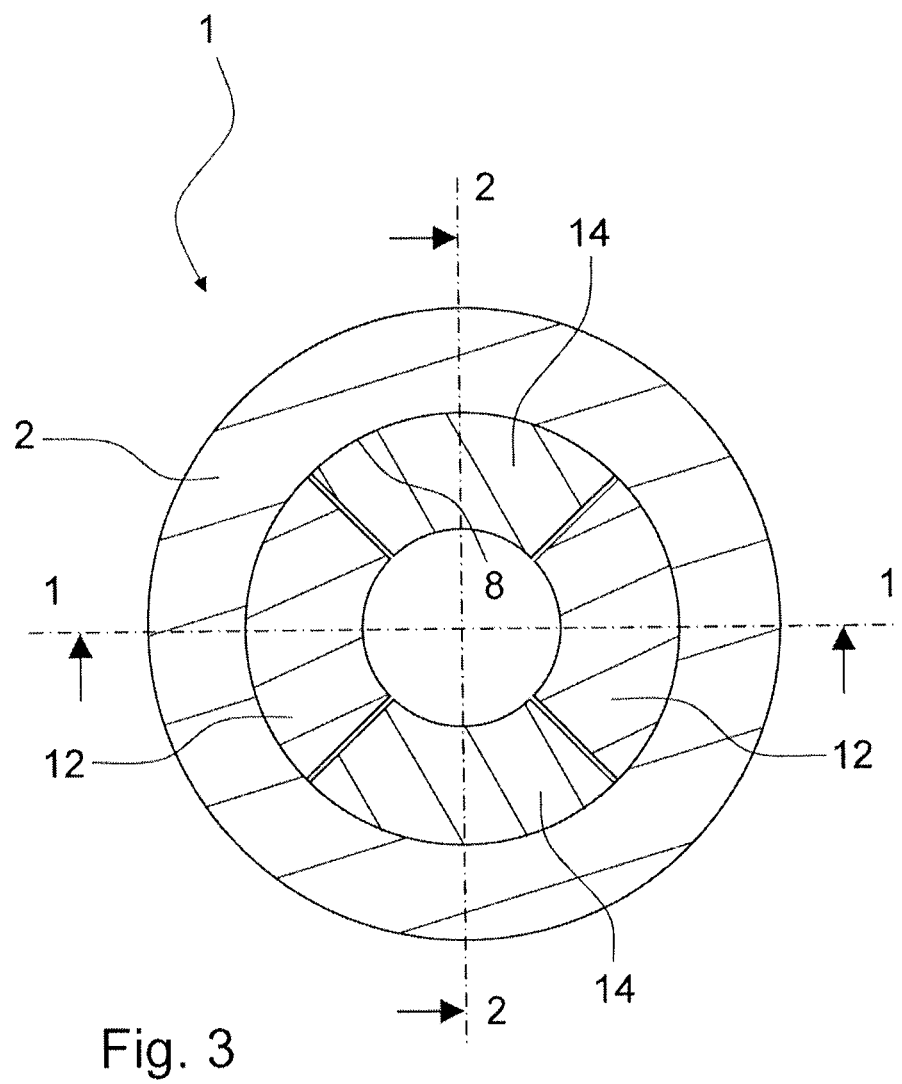
FIG. 3 illustrates a section according to line 3-3 in FIG. 1 or in FIG. 2.

FIGS. 1 to 3 illustrate different sections of a stopcock 1 having a housing 2, which encloses an axis 3 in a substantially tubular manner.

Sitting concentrically to the axis 3 is a plug 4 that sits with an outer conical surface 5 in a conical seat 6 of the housing 2. The large surface area of this snugly-fitting seat is used for sealing. The housing 2 is penetrated by a channel 7 which also penetrates through the plug 4 in a portion 7' and travels outside of the stopcock 1 into an endoscope 13. In the rotational position in FIG. 1, the channels 7 and 7' are aligned. The stopcock 1 is thus open. If the plug 4 is rotated, then the channel 7 can be closed.

Adjacent to the conical seat 6, a bearing collar 8 into which a part of the plug 4 extends is configured in the housing 1. In this bearing collar 8, a handle body 9 having a cylindrical outer surface concentric to the axis 3 is also rotatably mounted. A handle 10 used for rotational actuation of the handle body 9 is fixed on the end face of the handle body 9 facing away from the plug.

The handle body 9 is separated from the plug 4, and configured so as to be displaceable relative thereto in the direction of the axis 3. A coil spring 11 configured so as to be concentric to the axis 3 is arranged between the handle body 9 and the plug 4, and pushes these two parts apart from one another in the direction of the axis 3.

FIG. 3 illustrates a section according to line 3-3 in FIGS. 1 and 2, i.e., at half the height between the plug 4 and the handle body 9, in the region in which the plug and handle body are in a rotational engagement that permits longitudinal displacement but prevents relative rotation. FIG. 3 indicates that in the region of the bearing collar 8, the housing 2 has arranged therein four fingers of which two fingers 12 are fixed to the plug 4 while two fingers 14 are fixed to the handle body 9.

FIGS. 1, 2, and 3 illustrate the interlocking of the fingers 12, 14, which—as illustrated in FIG. 3—are configured with little freedom of movement in the direction of rotation, in order to ensure a precise rotational coupling. The fingers 12, 14 also allow for longitudinal displacement of the plug 4 relative to the handle body 9, whereupon the fingers 12 are moved with the plug 4 and the fingers 14 are moved with the handle body 9.

FIGS. 1 and 2 illustrate the housing 2 and the handle body 9 in a position that is locked in the direction of the axis 3. This locking is achieved by a snap ring 16, which is configured so as to be resiliently stretchable in the usual manner and—as shown in FIGS. 1 and 2—lies partially in an inner groove 17 in the bearing collar 8 and partially in an outer groove 18 in the outer surface of the handle body 9. At this position, according to FIG. 3, the handle body 9 is present in the form of the fingers 14 only in partial circumferential regions. The outer groove 18 is thus configured in the fingers 14 and retains the snap ring 16 there.

Sitting therebetween are the fingers 12 of the plug 4, the exact shape of which is depicted in FIG. 1. At the free ends of the fingers 12, a respective cam 19 is configured, which has a run-on slope 20 toward two directions when viewed in the direction of the axis 3.

At the end of the plug 4 lying opposite to the handle body 9, the plug is provided with an axial projection 22 that protrudes out from the housing 2 in the extension of the conical seat 6 through an opening. If pressure is applied to the projection 22 in the direction of the arrow 23, then the plug 4 is moved in the direction of the handle body 9. The cams 19 arrive with the oblique run-on surfaces 20 thereof against the inner side of the snap ring 16 and press the snap ring with outward spreading into the inner groove 17 in the housing 2. This releases the axial barrier effect between the handle body 9 and the housing 2. The handle body 9 can now be pressed out freely from the housing 2 in the direction of the axis, and so can the plug 4 thereof. The stopcock 1 is then therewith completely dismantled.

Assembly after subsequently cleaning and disinfection is very simple. The spring 11 is arranged between the handle body 9 and the plug 4, which are then interlocked with the fingers 12, 14 as shown in FIG. 3. The snap ring 16 is placed in the inner groove 17.

The assembled unit of the plug 4, spring, 11, and handle body 9 is subsequently inserted into the housing 2 in the direction of the axis 3. The run-on slopes 20 of the cams 19 then arrive against the snap ring 16 and spread same out, until the snap ring can allow the cams to pass. The installation position according to FIGS. 1 and 2 is then achieved.

LIST OF REFERENCE SIGNS

1 Stopcock
2 Housing
3 Axis
4 Plug
5 Conical surface
6 Conical seat
7 Channel
8 Bearing collar
9 Handle body
10 Handle
11 Coil spring
12 Finger (plug)
13 Endoscope
14 Finger (handle)
16 Snap ring
17 Inner groove
18 Outer groove
19 Cam
20 Run-on slope
22 Projection
23 Arrow

The invention claimed is:

1. A stopcock for a channel that guides a flux medium in a medical endoscope, the stopcock having a housing that accommodates a plug so as to be rotatable about an axis thereof in a conical seat penetrated by the channel, wherein:
the housing has a bearing collar adjacent to the conical seat in the direction of the axis, wherein a handle body is mounted in the bearing collar so as to be rotatable about the axis, the handle body supporting a handle outside the housing and being rotationally coupled to the plug so as to be displaceable in the direction of the axis and also being resiliently supported relative thereto,
the handle body has a radially elastic detent device that engages a circumferential inner groove of the bearing collar so as to be locking in the direction of the axis,
the plug is arranged and configured so as to release the engagement of the detent device between the handle body and the bearing collar upon displacement in the direction of the axis into an unlocked position,
the detent device is configured as a snap ring mounted in a circumferential outer groove of the handle body, and
the plug supports a plurality of cams that are arranged so as to be circumferentially distributed and extend radially outward, and that, in the unlocked position of the plug, arrive at engagement at the snap ring causing an expansion that the snap ring is spread out of engagement with the outer groove of the handle body.

2. The stopcock according to claim 1, wherein the cams sit at the free ends of fingers arranged between fingers of the handle body so as to extend out from the plug in the direction of the handle body.

3. The stopcock according to claim 2, wherein the cams have run-on slopes in both directions of displacement.

4. The stopcock according to claim 1, wherein the cams have run-on slopes in both directions of displacement.

5. The stopcock according to claim 1, wherein the unlocked position is provided such that the handle body and the bearing collar are disengaged through a movement of the plug in a reverse direction that is opposite an insertion direction along the axis of the stopcock.

* * * * *